United States Patent
Li et al.

(10) Patent No.: US 8,405,024 B2
(45) Date of Patent: Mar. 26, 2013

(54) ION MOBILITY SPECTROMETER

(75) Inventors: Yuanjing Li, Beijing (CN); Qingjun Zhang, Beijing (CN); Hua Peng, Beijing (CN); Yangtian Zhang, Beijing (CN)

(73) Assignee: Nuctech Company Limited, Beijing (CN)

( * ) Notice: Subject to any disclaimer, the term of this patent is extended or adjusted under 35 U.S.C. 154(b) by 52 days.

(21) Appl. No.: 13/000,337

(22) PCT Filed: Jul. 6, 2009

(86) PCT No.: PCT/CN2009/072646
§ 371 (c)(1),
(2), (4) Date: Dec. 20, 2010

(87) PCT Pub. No.: WO2010/006536
PCT Pub. Date: Jan. 21, 2010

(65) Prior Publication Data
US 2011/0114837 A1    May 19, 2011

(30) Foreign Application Priority Data
Jul. 16, 2008  (CN) .......................... 2008 1 0116735

(51) Int. Cl.
*H01J 49/40* (2006.01)
(52) U.S. Cl. ..................................................... 250/286
(58) Field of Classification Search .................. 250/286, 250/287
See application file for complete search history.

(56) References Cited

U.S. PATENT DOCUMENTS 6,642,513 B1  11/2003  Jenkins et al.
7,511,268 B2 *  3/2009  Landgraf ...................... 250/288

FOREIGN PATENT DOCUMENTS

| CN | 2826425 Y | 10/2006 |
| CN | 1916619 A | 2/2007 |
| CN | 2886569 Y | 4/2007 |
| CN | 201247223 Y | 5/2009 |
| WO | 2004102611 A2 | 11/2004 |
| WO | 2006129101 A1 | 12/2006 |

OTHER PUBLICATIONS

International Search Report for PCT/CN2009/072646 (5 pages), Oct. 1, 2009.

* cited by examiner

*Primary Examiner* — Kiet T Nguyen
(74) *Attorney, Agent, or Firm* — SNR Denton US LLP

(57) ABSTRACT

Disclosed is an ion mobility spectrometer. The ion mobility spectrometer comprises a sample injector (14), a semipermeable membrane (15), an ionization region (16), a terminal electrode (18), an ion storage region, a drift region and a Faraday plate (22), which are arranged along a drift tube in turn, wherein one or more air inlets (29) connected with a needle valve (30) and a first filtering device (31) are arranged in one side near the semipermeable membrane (15) of the ionization region (16), there is at least one opening in the terminal electrode (18), whose diameter is smaller than the diameter of the air inlets (29), an air outlet (28) connected with an air extracting pump (27) is arranged near the terminal electrode (18) in the ionization region (16), the drift region is separated from the ionization region (16) by a micropore structure of the ion storage region, another air outlet (25) connected with another air extracting pump (26) is arranged at one side near the Faraday plate (22) of the terminal electrode (18).

7 Claims, 2 Drawing Sheets

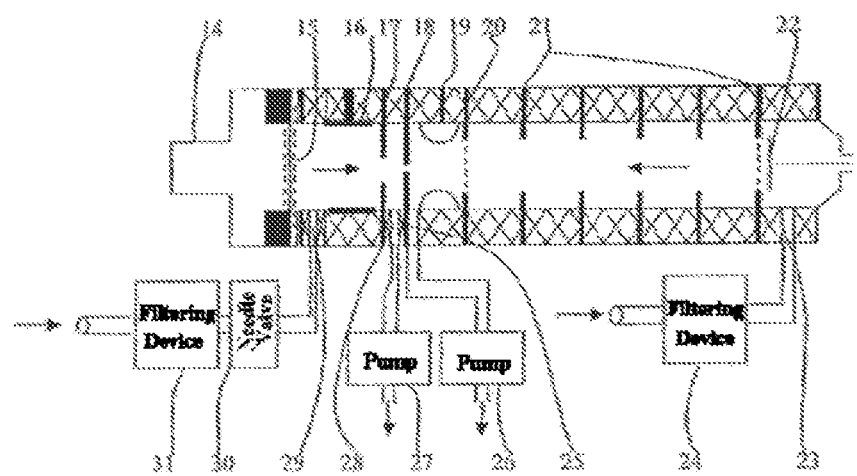
Fig.2
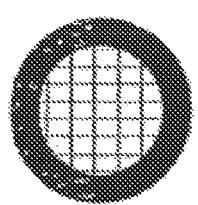 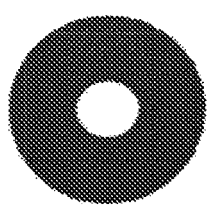 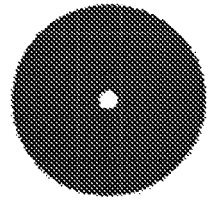 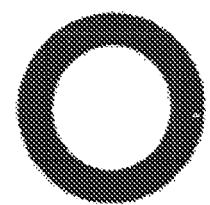
Fig.3A  Fig.3B  Fig.3C  Fig.3D

ION MOBILITY SPECTROMETER

CROSS REFERENCE TO RELATED APPLICATIONS

This is a NATIONAL STAGE under 35 USC 371 of and claims priority to International Application PCT/CN2009/072646, filed 6 Jul. 2009, which claims priority to CN 200810116735.5, filed 16 Jul. 2008.

BACKGROUND OF THE INVENTION

1. Field of Invention

The present invention relates to an inspection device for detecting drugs and explosives utilizing the ion mobility technique, in the security detection field, and in particular to an ion mobility spectrometer (IMS) capable of effectively promoting sample injection efficiency.

2. Description of Prior Art

The ion mobility spectrometer (IMS) effect identifies ions based on different drifting speeds of different ions in a uniform weak electric field, and is generally constituted by a sample injection section, an ionization section, an ion gate, a drift region, a collection region, a reading circuit, a data collection and process section, and a control section and the like.

In the prior art, a semipermeable membrane is employed so that it makes the environment cleanliness level required by the IMS lower. A negative pressure is formed by designing and adjusting appropriate air flow speeds on both sides of the semipermeable membrane, however, the effect of the negative pressure is limited to a certain degree and thus the sample injection efficiency remains low.

Chinese patent document CN1916619A discloses an ion mobility spectrometer based on sample injection of a membrane, which utilizes a micro-pump coupled in series between the semipermeable membrane and the ionization region to form negative pressure, increasing the permeation rate of the semipermeable membrane. However, since the micro-pump is coupled in series in the system, and most drugs and explosives as well as the semipermeable membrane per se need work at the temperature above 100 degrees, such as 180 degrees, which is high for the micro-pump that cannot run continuously and steadily at the high temperature, the application and the service life of the IMS are limited to a certain degree. Moreover, the interior structure of the micro-pump is easily polluted and difficult to clean, resulting in performance degradation of the IMS.

Referring to FIG. 1, another structure employed in the prior art includes a sample injector 1, a semipermeable membrane 2, an ion source 3, an ion gate 4, a ring electrode 5, and a Faraday plate 6 which are arranged along a drift tube in turn, and further includes an air extracting pump 10 connected with an opening 9, a filtering device 12 connected with an opening 11, and a filtering device 8 connected with an opening 7. The ambient air flows through the filtering device 12 and then enters the ionization region through an aperture 13 near the semipermeable membrane 2, and forms high-speed air flow near the semipermeable membrane 2 so as to form such an air pressure difference between the opposite sides of the semipermeable membrane 2 that the molecules to be detected will be introduced. The migrant air enters the drift region through the filtering device 8, and is extracted out of the drift tube along with the reaction air through the pump 10. The problem in the above described prior art is that a controllable low air pressure is formed at the side of the semipermeable membrane which causes the sample injection efficiency of the semipermeable membrane to be reduced.

SUMMARY OF THE INVENTION

In view of the above problems in the prior art, an object of the present invention is to provide a solution for promoting the sample injection efficiency of an IMS, which is capable of increasing the sample injection efficiency effectively.

According to an aspect of the present invention, there is provided an ion mobility spectrometer (IMS) comprising a sample injector, a semipermeable membrane, an ionization region and a terminal electrode which are arranged along a drift tube in turn, wherein one or more air inlets connected with a needle valve and a first filtering device for intaking air are arranged on one side of the ionization region adjacent to the semipermeable membrane, at least one opening is arranged in the terminal electrode, whose diameter is smaller than the diameter of the air inlets, and an air outlet connected with an air extracting pump for extracting air is arranged in the ionization region adjacent to the terminal electrode.

Preferably, the IMS further comprises a focusing electrode positioned near to one side of the ionization region, which focuses the ions formed in the ionization region so that the ions pass through the opening in the terminal electrode.

Preferably, the focusing electrode has an opening with an interior diameter larger than that of the opening of the terminal electrode.

Preferably, the IMS further comprises: a drift region arranged at one side of the terminal electrode away from the sample injector; and a Faraday plate arranged at the end of the drift region; wherein one or more openings arranged at the Faraday plate are connected with a second filtering device.

Preferably, the IMS further comprises another air outlet arranged at one side of the terminal electrode near to the Faraday plate, wherein another air outlet is connected with another air extracting pump.

Preferably, the semi-permeable membrane, the ionization region, the focusing electrode and the drift region are all air-tight except for the openings.

Preferably, the IMS further comprises two meshed metal sheets for clamping the semipermeable membrane therebetween.

According to another aspect of the present invention, there is provided an ion mobility spectrometer (IMS) comprising a sample injector, a semipermeable membrane, an ionization region, a terminal electrode, an ion storage region, a drift region and a Faraday plate which are arranged along a drift tube, characterized in that the drift region is separated from the ionization region by a micropore structure of the ion storage region; an opening is arranged in the ionization region adjacent to the terminal electrode, the opening is connected with an air extracting pump for extracting air; and another air outlet is arranged at one side of the terminal electrode near to the Faraday plate, the another air outlet being connected with another air extracting pump.

Based on the above structure, the present invention can control the air flow speed of the pump coupled with the ionization region, and since larger air-resistance is formed by the micropore structure and the needle valve, lower air pressure is formed at the ionization region and the semipermeable membrane, so as to promote largely the permeation rate of the semipermeable membrane.

Since the drift region is coupled independently with a pump and is separated from the ionization region by a micropore structure of the ion storage region, a smaller negative or positive pressure relative to the ambient pressure can be formed in the drift region, which does not affect the drift of the ions and lowers the sealing requirement level of the drift tube.

Due to the structure of the semipermeable membrane with both sides thereof clamped by two metal meshed sheets, the semipermeable membrane will not protrude due to the low air pressure.

Due to the utilization of the focusing electrode, the ions can be introduced into the storage region through the micropore, which does not reduce the amount of the ions stored.

BRIEF DESCRIPTION OF THE DRAWINGS

The above advantages and features of the present invention will be more apparent from the following detailed description taken conjunction with the drawings in which:

FIG. 2 is a schematic structure view of an ion mobility spectrometer according to an embodiment of the present invention; and FIGS. 3A-3D are a schematic view of the electrodes used in the ion mobility spectrometer according to the embodiment of the present invention.

DETAILED DESCRIPTION OF THE PREFERRED EMBODIMENTS

Figure 1:
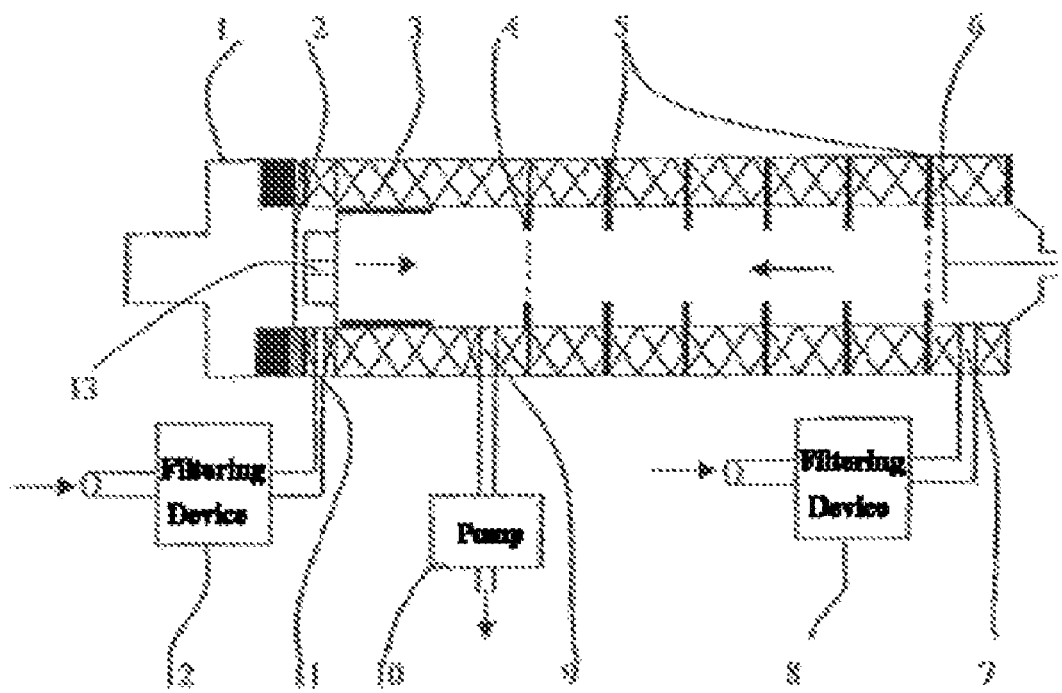
FIG. 1 is a schematic structure view of an ion mobility spectrometer of the prior art.

Hereafter, a detailed description will be given of the preferred embodiments of the present invention with reference to the figures, throughout which like reference signs denote identical or similar components, though illustrated in different figures. For the sake of clarity and conciseness, specific description of any known function or structure incorporated herein will be omitted lest the subject of the present invention be obscured.

Referring to FIGS. 2 and 3, the structure of an IMS according to the present invention includes, arranged sequentially along a drift tube, a sample injector 14, a semipermeable membrane 15 with both sides thereof clamped by metal meshed sheets shaped as shown in FIG. 3A, an ionization region 16 with a micropore 29, a focusing electrode 17 with a central opening shaped as shown in FIG. 3B, an ion storage terminal electrode 18 with a micropore and with a central opening shaped as shown in FIG. 3C, a storage electrode 19 with a central opening shaped as shown in FIG. 3B, another terminal electrode 20 with meshes in the center shaped as shown in FIG. 3A, a ring electrode 21 with a central opening shaped as shown in FIG. 3D, a Faraday plate 22 and the like. An opening 25 is arranged between the terminal electrode 18 and the storage electrode 19.

At the opposite ends of the ionization region are respectively provided an air extracting pump 27 coupled with an opening 28, and a needle valve 30 and a filtering device 31 coupled with the micropore 29. At the opposite ends of the drift region are respectively provided a filtering device 24 coupled with an opening 23, and an air extracting pump 26 coupled with the opening 25. Both the micropore 29 and the micropore of the terminal electrode 18 should have interior diameters of smaller than 0.5 mm, and the interior diameter of the micropore of the terminal electrode 18 is slightly smaller than the interior diameter of the micropore 29. The reaction air enters the ionization region through the filtering device 31, the needle valve 30 and the micropore 29, and is extracted by the pump 27 out of the drift tube through the opening 28 between the focusing electrode 17 and the ion storage terminal electrode 18. The migrant air enters the drift region through the filtering device 24 and the opening 23, and is extracted by the pump 26 out of the drift tube through the opening 25 at the other opposite end of the drift region.

As such, due to the utilization of the needle valve 30 and the air extracting pump 27 dedicatedly used in the ionization region, as well as the micropore of the terminal electrode 18, a controllable low air pressure region is formed in the ionization region. The user can form the low air pressure region as required.

In addition, since the drift region is independently coupled with the pump 26 and is separated from the ionization region by the micropore structure of the ion storage terminal electrode, a smaller negative or positive pressure relative to the ambient pressure can be formed in the drift region, which does not affect the drift of the ions and lowers the sealing requirement level of the drift tube.

Moreover, due to the structure of the semipermeable membrane 15 with both sides thereof clamped by two metal meshed sheets, the semipermeable membrane 15 will not protrude due to the low air pressure. Further, due to the utilization of the focusing electrode 17, the ions can be introduced into the storage region through the central micropore of the terminal electrode 18, which will not reduce the amount of the ions stored.

The foregoing description is only intended to illustrate the embodiments of the present invention rather than limiting the present invention. It will be appreciated by those skilled in the art, that any modification or substitution that can be made without departing from the scope of the present invention should be construed to fall within the scope of the present invention. Therefore, the scope of the present invention should be defined by the claims and the equivalents thereof.

What is claimed is:

1. An ion mobility spectrometer, having a sample injector, a semipermeable membrane, an ionization region and a terminal electrode, which are arranged along a drift tube in turn, comprising:
    an air inlet connected with a needle valve and a first filtering device for intaking air arranged on one side of the ionization region adjacent to the semipermeable membrane;
    at least one opening provided in the terminal electrode, whose diameter is smaller than a diameter of the air inlet;
    a first air outlet connected with an air extracting pump for extracting air and provided in the ionization region adjacent to the terminal electrode; and
    an ion mobility spectrometer having two meshed metal sheets for clamping the semi-permeable membrane therebetween.

2. The ion mobility spectrometer of claim 1, further comprising a focusing electrode positioned near to one side of the ionization region, which focuses ions formed in the ionization region so that the ions pass through the opening in the terminal electrode.

3. The ion mobility spectrometer of claim 2, wherein the focusing electrode has an opening with a diameter larger than that of the opening of the terminal electrode.

4. The ion mobility spectrometer of claim 2, wherein the semipermeable membrane, the ionization region, the focusing electrode and a drift region are air-tight except for the openings.

5. The ion mobility spectrometer of claim 1, further comprising:
    a drift region arranged at one side of the terminal electrode in which the side is away from the sample injector; and
    a Faraday plate arranged at an end of the drift region, wherein an opening arranged at the Faraday plate is connected with a second filtering device.

6. The ion mobility spectrometer of claim 1 or 5, further comprising a second air outlet arranged at one side of the terminal electrode and in an ion storage region, wherein the second air outlet is connected with another air extracting pump.

7. An ion mobility spectrometer comprising a sample injector, a semipermeable membrane, an ionization region, a terminal electrode, an ion storage region, a drift region and a storage region, which are arranged along a drift tube, comprising:

the drift region separated from the ionization region by a micropore structure of the ion storage region;

an opening arranged in the ionization region adjacent to the terminal electrode, the opening being connected with an air extracting pump for extracting air; and another air outlet arranged at one side of the terminal electrode and in an ion storage region, the another air outlet is connected with another air extracting pump.

* * * * *

UNITED STATES PATENT AND TRADEMARK OFFICE
CERTIFICATE OF CORRECTION

PATENT NO. : 8,405,024 B2
APPLICATION NO. : 13/000337
DATED : March 26, 2013
INVENTOR(S) : Yuanjing Li et al.

Page 1 of 1

It is certified that error appears in the above-identified patent and that said Letters Patent is hereby corrected as shown below:

On the Title Page

Item (73) Assignee should read:
NUCTECH COMPANY LIMITED (BEIJING, CN) and TSINGHUA UNIVERSITY (BEIJING, CN).

Item (30) Foreign Application Priority Data should read:
July 16, 2008 (CN) …… 200810116735.5.

Signed and Sealed this
First Day of October, 2013

Teresa Stanek Rea
*Deputy Director of the United States Patent and Trademark Office*